(12) United States Patent
Sommer, Jr.

(10) Patent No.: US 9,234,838 B2
(45) Date of Patent: *Jan. 12, 2016

(54) METHOD TO IMPROVE DETECTION OF THIN WALLED POLYETHYLENE TEREPHTHALATE CONTAINERS FOR RECYCLING INCLUDING THOSE CONTAINING LIQUIDS

(71) Applicant: National Recovery Technologies, LLC, Nashville, TN (US)

(72) Inventor: Edward J. Sommer, Jr., Nashville, TN (US)

(73) Assignee: National Recovery Technologies, LLC, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/033,481

(22) Filed: Sep. 22, 2013

(65) Prior Publication Data

US 2014/0299524 A1 Oct. 9, 2014

Related U.S. Application Data

(63) Continuation-in-part of application No. 14/033,445, filed on Sep. 21, 2013.

(60) Provisional application No. 61/853,572, filed on Apr. 8, 2013.

(51) Int. Cl.
*B07C 5/00* (2006.01)
*G01N 21/3563* (2014.01)
*B07C 5/34* (2006.01)
*G01N 29/36* (2006.01)
*G01N 21/359* (2014.01)
*G01N 21/90* (2006.01)

(52) U.S. Cl.
CPC .......... *G01N 21/3563* (2013.01); *B07C 5/3408* (2013.01); *G01N 21/359* (2013.01); *G01N 29/36* (2013.01); *G01N 21/9081* (2013.01); *G01N 2223/05* (2013.01)

(58) Field of Classification Search
CPC .......................... G01N 2223/05; G01N 29/36
USPC .................. 209/576, 577, 587, 588
See application file for complete search history.

(56) References Cited

U.S. PATENT DOCUMENTS

| | | | |
|---|---|---|---|
| 4,090,074 A | 5/1978 | Watt et al. |
| 4,377,392 A | 3/1983 | Massey et al. |
| 4,486,894 A | 12/1984 | Page et al. |
| 4,626,688 A | 12/1986 | Barnes |

(Continued)

OTHER PUBLICATIONS

D.M. Scott; "A two-colour near-infrared sensor for sorting recycled plastic waste"; Measurement Science and Technology; vol. 6; No. 6; Jan. 1, 1995; pp. 156-159; UK.

(Continued)

*Primary Examiner* — Howard Sanders
(74) *Attorney, Agent, or Firm* — Frost Brown Todd LLC

(57) ABSTRACT

Disclosed herein are methods to improve detection of PET polymer materials within a waste material to be sorted. The methods disclosed allow for municipal solid waste to be separated so that PET polymer materials, including those containing liquids, are separated for recycling, or other purposes. PET polymer materials, such as water bottles which have been disposed of while still containing liquid may now be separated by the enhanced methods disclosed herein.

12 Claims, 14 Drawing Sheets

(56) References Cited

U.S. PATENT DOCUMENTS

| | | |
|---|---|---|
| 4,848,590 A | 7/1989 | Kelly |
| 5,141,110 A * | 8/1992 | Trischan ............... B07C 5/3416 209/3.1 |
| 5,176,260 A | 1/1993 | Oder |
| 5,305,893 A | 4/1994 | Hereford |
| 5,676,256 A | 10/1997 | Kumar et al. |
| 5,738,224 A | 4/1998 | Sommer, Jr. et al. |
| 5,818,899 A | 10/1998 | Connolly et al. |
| 5,841,832 A | 11/1998 | Mazess et al. |
| 5,841,833 A | 11/1998 | Mazess et al. |
| 5,931,308 A | 8/1999 | Gesing et al. |
| 5,966,217 A * | 10/1999 | Roe ........................ G01N 21/31 209/524 |
| RE36,537 E | 2/2000 | Sommer, Jr. et al. |
| 6,060,677 A | 5/2000 | Ulrichsen et al. |
| 6,122,343 A | 9/2000 | Pidcock |
| 6,128,365 A | 10/2000 | Bechwati et al. |
| 6,266,390 B1 | 7/2001 | Sommer, Jr. et al. |
| 6,272,230 B1 | 8/2001 | Hiraoglu et al. |
| 6,338,305 B1 | 1/2002 | McHenry et al. |
| RE37,536 E | 2/2002 | Barnes |
| 6,353,197 B1 | 3/2002 | Ulrichsen et al. |
| 6,399,951 B1 | 6/2002 | Paulus et al. |
| 6,519,315 B2 | 2/2003 | Sommer, Jr. et al. |
| 6,545,240 B2 | 4/2003 | Kumar |
| 6,587,575 B1 | 7/2003 | Windham et al. |
| 6,610,981 B2 | 8/2003 | Sommer, Jr. et al. |
| 6,661,867 B2 | 12/2003 | Mario et al. |
| 6,855,901 B1 | 2/2005 | Guenard et al. |
| 6,888,917 B2 | 5/2005 | Sommer, Jr. et al. |
| 7,012,256 B1 | 3/2006 | Roos et al. |
| 7,099,433 B2 | 8/2006 | Sommer, Jr. et al. |
| 7,200,200 B2 | 4/2007 | Laurila et al. |
| 7,244,941 B2 | 7/2007 | Roos et al. |
| 7,262,380 B1 | 8/2007 | Ulrichsen et al. |
| 7,286,634 B2 | 10/2007 | Sommer, Jr. et al. |
| 7,356,115 B2 | 4/2008 | Ford et al. |
| 7,542,873 B2 | 6/2009 | Vince et al. |
| 7,558,370 B2 | 7/2009 | Sommer, Jr. et al. |
| 7,564,943 B2 | 7/2009 | Sommer, Jr. et al. |
| 7,664,225 B2 | 2/2010 | Klein |
| 7,816,616 B2 | 10/2010 | Kenny et al. |
| 7,848,484 B2 | 12/2010 | Sommer, Jr. et al. |
| 2004/0066890 A1 | 4/2004 | Dalmijn et al. |
| 2006/0070928 A1 | 4/2006 | Lovhaugen et al. |
| 2008/0169225 A1 | 7/2008 | De Greef |
| 2010/0185319 A1 | 7/2010 | Petzoid |
| 2011/0116596 A1 | 5/2011 | Sommer, Jr. et al. |

OTHER PUBLICATIONS

Hamed Masoumi, et al.; "Identification and Classification of Plastic Resins using Near Infrared Reflectance Spectroscopy"; Proceedings of World Academy of Science, Engineering and Technology; International Science Index; vol. 6; No. 5; May 22, 2012; pp. 141-147.

* cited by examiner

METHOD TO IMPROVE DETECTION OF THIN WALLED POLYETHYLENE TEREPHTHALATE CONTAINERS FOR RECYCLING INCLUDING THOSE CONTAINING LIQUIDS

This application is a continuation-in-part application of co-pending U.S. patent application Ser. No. 14/033,445, filed Sep. 21, 2013, entitled "Method to Improve Detection of Thin Walled Polyethylene Terephthalate Containers for Recycling Including Those Containing Liquids," which is hereby incorporated by reference in its entirety, which claims benefit of U.S. Provisional Patent Application Ser. No. 61/853,572, filed Apr. 8, 2013, entitled "Method to Improve Detection of Thin Walled PET Containers for Recycling Including those Containing Liquids" which is hereby incorporated by reference in its entirety.

STATEMENT REGARDING FEDERALLY SPONSORED RESEARCH OR DEVELOPMENT

Not applicable.

BACKGROUND OF THE INVENTION

Municipal solid waste (MSW) is an ever growing segment of our society that requires daily attention to maintain a healthy environment for our cities, towns, and the countryside. Past practices focused on burying the waste in the many landfills located outside population centers around the country. In today's society there are significant processes in place to reduce the amount of MSW going into these landfills to extend landfill life, reduce costs, and reduce adverse impacts of landfills on the environment. Significant among these processes are extraction and recycling of recyclable materials from MSW, production of compost from food waste and fiber streams, and in some cases incineration of portions of the MSW to reduce waste volume and to generate recoverable energy.

Today manufacturing of plastic bottles from polyethylene terephthalate (PET) for use in food packaging is widespread and growing. PET bottles are widely used worldwide to bottle both carbonated and still beverages. The bottles are favored by food and drink manufacturers for many reasons, among them PET bottles have clear walls so the contents are easily seen by the consumer, they are very tough and strong, and they have long shelf life for maintenance of carbonation. PET containers are well-suited for recycling. They are among the most expensive of packaging plastics and can provide substantial revenues for processes that recover and sale recyclables from the municipal waste stream. The recovery of used PET containers for use as a recycled material depends greatly upon the ability of automated sorting systems in use at today's materials recycling facilities (MRF's) to detect, identify, and segregate the used PET bottles from the municipal solid waste stream (MSW). There are several manufacturers of such automated sorting systems such as National Recovery Technologies LLC (Nashville, Tenn.), MSS, Inc. (Nashville, Tenn.), Titech (Akershus, Norway), Pellenc (Pertuis, France), and BT-Wolfgang Binder GmbH (Gleisdorf, Austria) most incorporating near infrared spectroscopic detection systems. Sorting systems from these vendors are in operation in industry for recovering PET plastics from MSW. However in recent years there has been a trend in industry to make the walls of PET beverage bottles thinner in order to reduce cost and lessen environmental impacts which causes problems for these sorting systems.

Thin walled PET containers are more difficult to detect and identify within the waste stream than are thicker walled containers due to the relatively small amount of PET material they incorporate. PET bottles for containing still water do not need to maintain carbonation and their walls in many cases have become very thin. PET bottles are a preferred package for still water bottling and particularly in individual serving sizes of about 16 oz and less, often referred to as single serving size. As it turns out many of these single serving sized thin walled PET bottles in addition to other PET bottles are discarded into the waste stream with their caps screwed on tightly and containing varying amounts of water or other liquid from just a trace to nearly full. It is not unusual to see bottles in the waste stream that are filled to ⅛, ¼, ½ and even more of capacity. These discarded PET bottles containing liquid are sometimes referred to in the recycling industry as "wet PET". Water, and for that matter any liquid, will interfere with the infrared detection systems of modern automated sorters rendering these partially filled containers harder to detect. The general condition of the waste offers unique problems that need to be solved.

Near infrared (NIR) based sorting systems used in today's industry sense in the range of about 800 nm to 2400 nm and typically operate either in reflection mode or in transmission mode. In reflection mode broad band NIR radiation is often employed to be reflected off the surface of the material being analyzed (the sample—in this case it would be a packaging container). As the NIR radiation interacts with the sample surfaces energy to varying degrees is absorbed from the radiation at certain wavelengths, the amount of radiation absorbed and at which wavelengths being characteristic to the sample chemistry. The NIR radiation that is reflected is comprised of the original energy spectrum of broadband wavelengths of the impinging NIR radiation less energy absorbed at the characteristic wavelengths of the sample chemistry. These absorption features contained in the reflected radiation are detected by near infrared sensors positioned to receive the reflected NIR radiation and are analyzed by computerized detection algorithms to identify a sample according to its chemistry. For example NIR sorters can distinguish among the varying packaging polymers found in the municipal waste stream such as polyethylene terephthalate (PET), polyethylene (PE), polyvinylchloride (PVC), polypropylene (PP), polystyrene (PS), and others, and sort them accordingly. Processing PET polymer materials requires procedures that exploit these physical characteristics in order to allow for the separation and isolation which is desired. The need is great for enhancing existing processing methods.

SUMMARY OF THE INVENTION

The present invention provides a method of improving detection of polyethylene terephthalate polymer materials within a stream of materials. The method includes the steps of providing a stream of materials; irradiating the stream of materials with near infrared radiation; measuring near infrared radiation emanating from the stream of materials; analyzing the measured near infrared radiation at two or more wavelength regions; determining a ratio of measured near infrared radiation at two regions of wavelengths; comparing the ratio to a preset threshold; adjusting the measured near infrared radiation measurements at one of the wavelength regions according to the results of the comparing step; processing the adjusted near infrared radiation measurements; and identifying at least one polyethylene terephthalate polymer material. In certain embodiments, the stream of materials contains at least one material item of polyethylene terephthalate polymer. In still other embodiments, the wavelength regions include a region located at about 1660 nm. In yet other embodiments, the ratio is determined for wavelength regions including a region located at about 1660 nm. In still other embodiments, adjusting the measured near infrared radiation measurements further includes adjusting the near infrared radiation measurement for a region located at about 1660 nm. In certain embodiments, the wavelength regions include a region located at about 1730 nm. In other embodiments, the preset threshold is a value between 0.8 and 0.95. In yet other embodiments, the method further includes separating the identified polyethylene terephthalate polymer material from the stream of materials. In certain embodiments, the wavelength regions include a region located at about 1690 nm. In other embodiments, the preset threshold is a value between 0.8 and 0.95. Certain embodiments further include separating the identified polyethylene terephthalate polymer material from the stream of materials.

Accordingly, one provision of the invention is to provide methods of improving detection of polyethylene terephthalate polymer materials within a stream of materials.

DETAILED DESCRIPTION OF THE INVENTION

The present invention disclosed herein is a method of processing waste material to improve the detection of thin walled polyethylene terephthalate ("PET") polymer materials including those that contain a liquid. PET polymer materials, such as water bottles, are disposed of and contained within Municipal solid waste ("MSW"). MSW is a material that is difficult to process due to the wide spectrum of physical conditions that make up its content. Specifically, regarding PET polymer material, it is not uncommon for such bottles or containers to be disposed of with the caps screwed on tightly with some volume of liquid trapped inside. PET polymer containers containing liquid are referred to as "wet" PET. Detecting and sorting wet PET has been difficult as the liquid interferes with the infrared detection systems of modern automated sorters. Accordingly, processing partially filled PET containers requires a procedure which overcomes these physical characteristics in order to allow for the separation of PET polymer materials, which may then be recycled. The need is great for such an improved recycling method.

Improved detection and sorting of PET polymer material requires the ability to measure near infrared ("NIR") radiation transmitted through or reflected off materials at two or more wavelength regions. The method disclosed herein then requires determining the ratio of measured transmitted or reflected NIR radiation at two regions of wavelengths and then adjusting the measured NIR radiation measurements based upon a comparison of the ratio to a preset threshold. In certain embodiments of the present invention, the regions of wavelengths include a region located in the vicinity of 1660 nanometers ("nm") and a region located in the vicinity of 1730 nm. In other embodiments of the present invention, the regions of wavelengths include a region located in the vicinity of 1660 nm and a region located in the vicinity of 1690 nm. After comparing the ratio to preset thresholds (disclosed herein), the measured NIR radiation measurements are adjusted to improve the detection of PET polymer material. The preset thresholds, ratios, manner of comparison of the two, and manner of adjusting the measured NIR radiation measurements are disclosed herein.

Figure 1:
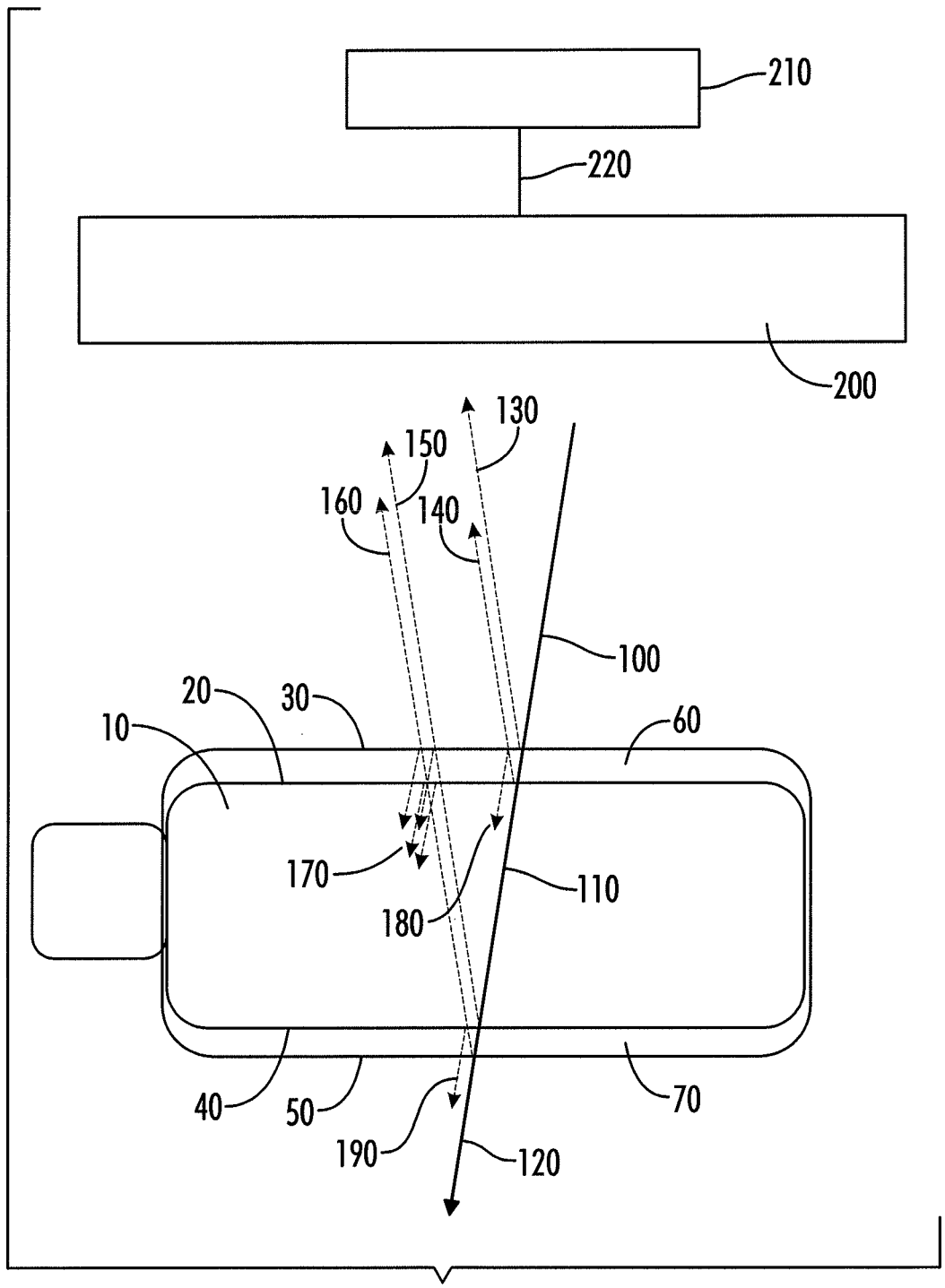
FIG. 1 depicts a schematic diagram showing the exemplary paths of near infrared radiation and the interaction of the same with a polyethylene terephthalate ("PET") container with regard to an embodiment of the present invention utilizing detection of near infrared radiation reflected at the various surfaces of the container.

Referring now to FIG. 1 wherein a configuration for measuring reflected NIR radiation is depicted, there is shown a depiction of the various reflections of NIR radiation coming off the walls of an empty packaging container, in this case a transparent PET container 10. The relative side wall thicknesses 60 and 70 of PET container 10 are exaggerated in the drawing for discussion purposes. Incident NIR radiation 100 emanating from a radiation source (not shown) which for reflective NIR detection is often deployed in the vicinity of detector system 200 strikes the first bottle wall 60 and passes through to the interior of the bottle as NIR radiation 110 which then passes through opposite bottle wall 70 and exits as transmitted NIR radiation 120. Automated sorting systems, which include a radiation source and detector system 200 are known in the art and readily commercially available, as described herein. At each interface of bottle wall a portion of incident radiation is reflected. For example reflected NIR radiation 130 reflects off the outer surface 30 of bottle wall 60 and picks up some NIR absorption information concerning the polymer chemistry of bottle wall 60. Reflected NIR radiation 140 reflects off the inner wall boundary 20 of wall 60 and carries rich NIR absorption information derived from two passes through the thickness of bottle wall 60. Similarly reflected NIR radiation 150 reflects off the inner wall boundary 40 of wall 70 picking up some NIR absorption information on the polymer chemistry of wall 70 plus rich NIR absorption information derived from two passes through wall 60. Reflected NIR radiation 160 is reflected off the outer wall boundary 50 of wall 70 and gains significant NIR absorption features from two passes through each of wall 60 and wall 70. Reflections 170, 180, and 190 are secondary reflections off the wall boundaries from interaction of the walls with primary reflected radiation and do not reach detection system 200. Reflected NIR radiations 130, 140, 150, and 160 are collected by NIR detector system 200 which sends energy and/or wavelength dispersive information about the reflected NIR radiations over connection 220 to computer analysis system 210 which runs an identification algorithm (not shown) to analyze the information and determine the polymer type of container 10. The computer analysis system 210 often also directs sorting mechanisms (not shown) which sort polymers according to the results of the identification algorithm. Computer analysis systems 210, also called computers, are well known in the industry and readily commercially available. Automated sorting systems, which are well known and readily commercially available, may include a computer analysis system 210 which runs an identification algorithm in order to perform the analysis step mentioned above. NIR radiations 140, 150, and 160 are particularly rich in information as they have passed through bottle walls twice, twice, and four times, respectively, thereby having significant interactions with polymer material so to enhance their NIR absorption features. In this respect NIR radiation 130 has one interaction at the bottle wall 60 surface, NIR radiation 140 has two passes through bottle wall 60. NIR radiation 150 has one interaction with bottle wall 70 surface and two passes through bottle wall 60, and NIR radiation 160 has two passes through bottle wall 60 and two passes through bottle wall 70. Summarizing, NIR radiations 130 and 140 emanating from radiation incidence upon the first bottle wall will carry NIR absorption information resulting from two passes through the bottle wall and one reflection off a wall surface. NIR radiations 150 and 160 carry NIR absorption information resulting from six passes through the bottle wall and one reflection off a wall surface. Together these four NIR radiations deliver polymer NIR absorption information to detection system 200 which detects and relays energy/wavelength dispersive information over connection 220 to computer analysis system 210.

Figure 13:
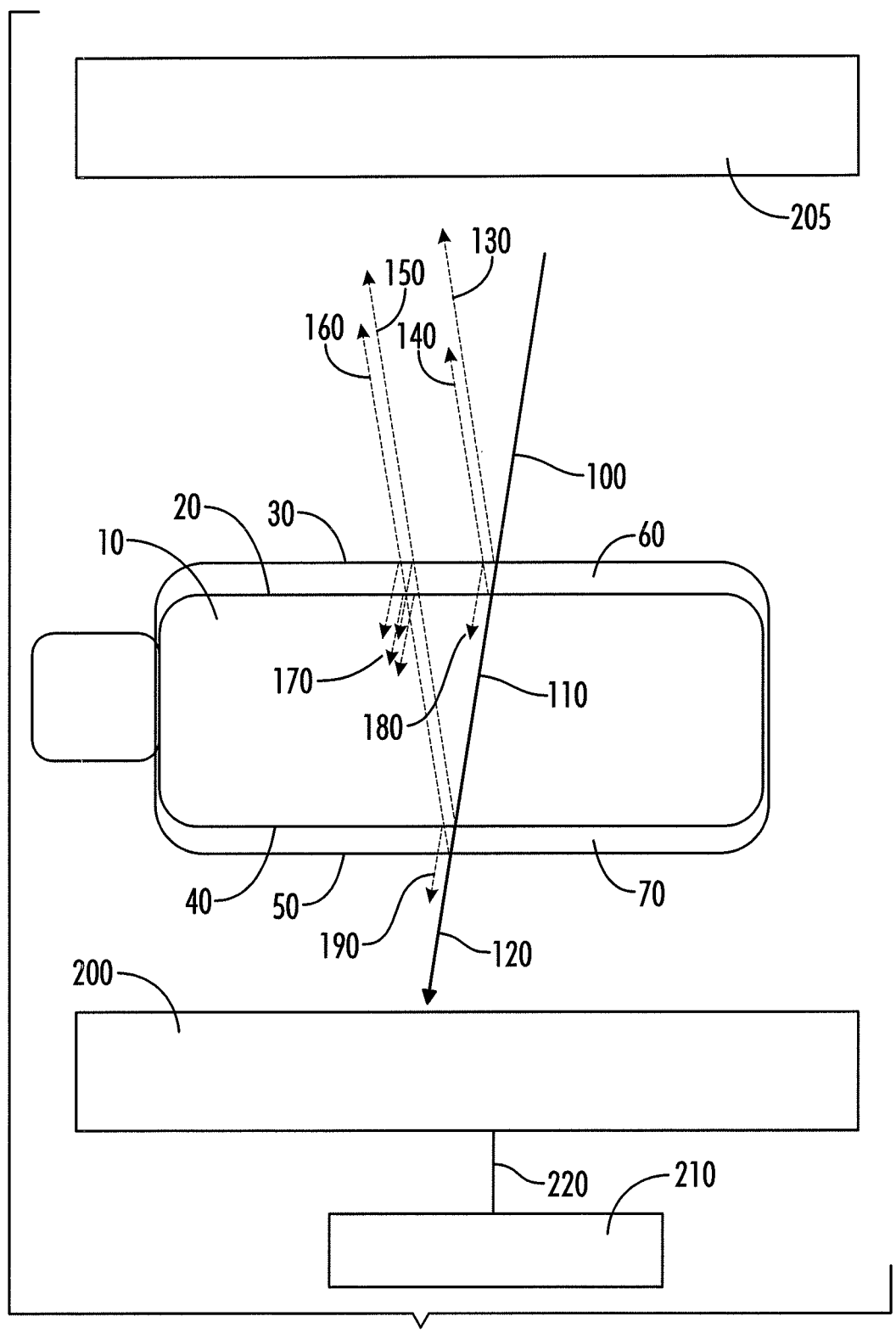
FIG. 13 depicts a schematic diagram showing the exemplary paths of near infrared radiation and the interaction of the same with a PET container with regard to an embodiment of the present invention utilizing detection of near infrared radiation transmitted through the walls of the container.

FIG. 13 shows a configuration for measuring NIR transmitted through container 10. In the transmissive case depicted incident radiation 100 emanates from NIR source 205. NIR detection system 200 is positioned so to receive transmitted NIR radiation 120 that passes through container 10 (whereas for the reflective case depicted in FIG. 1 it is positioned to receive reflected NIR radiations 130, 140, 150, and 160 from container 10). Transmitted NIR radiation 120 is rich in NIR absorption information pertaining to the chemistry of the walls 60 and 70 of the container 10 since it passes through the walls 60 and 70. NIR radiation 120 delivers polymer NIR absorption information to detection system 200 which detects and relays energy/wavelength dispersive information over connection 220 to computer analysis system 210

Figure 2:
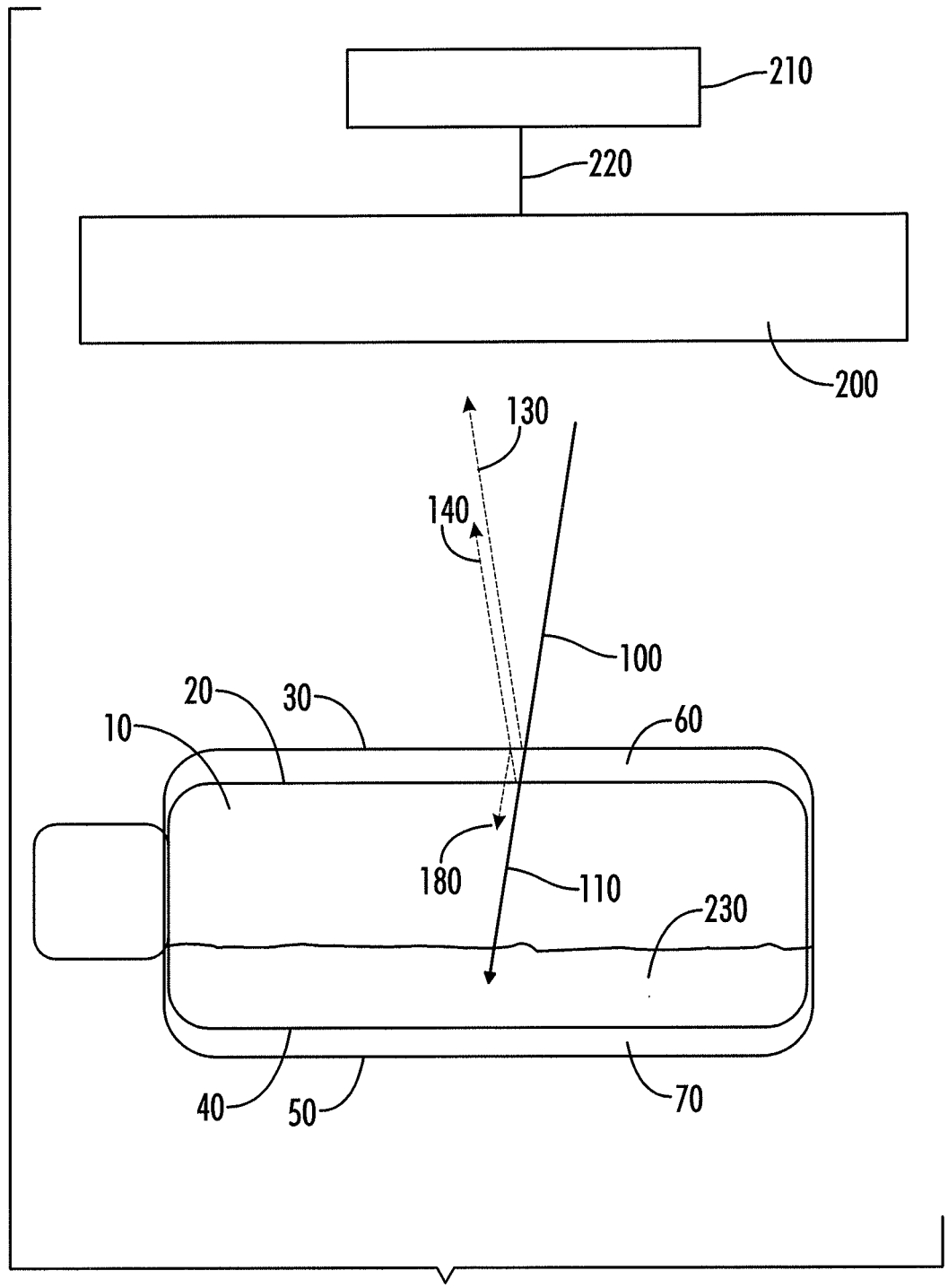
FIG. 2 depicts a schematic diagram similar to FIG. 1. The PET container shown in FIG. 2 contains a liquid, which alters the manner of interaction of the exemplary paths of near infrared radiation with the PET container in this embodiment of the present invention utilizing detection of near infrared radiation reflected at the various surfaces of the container.
Figure 14:
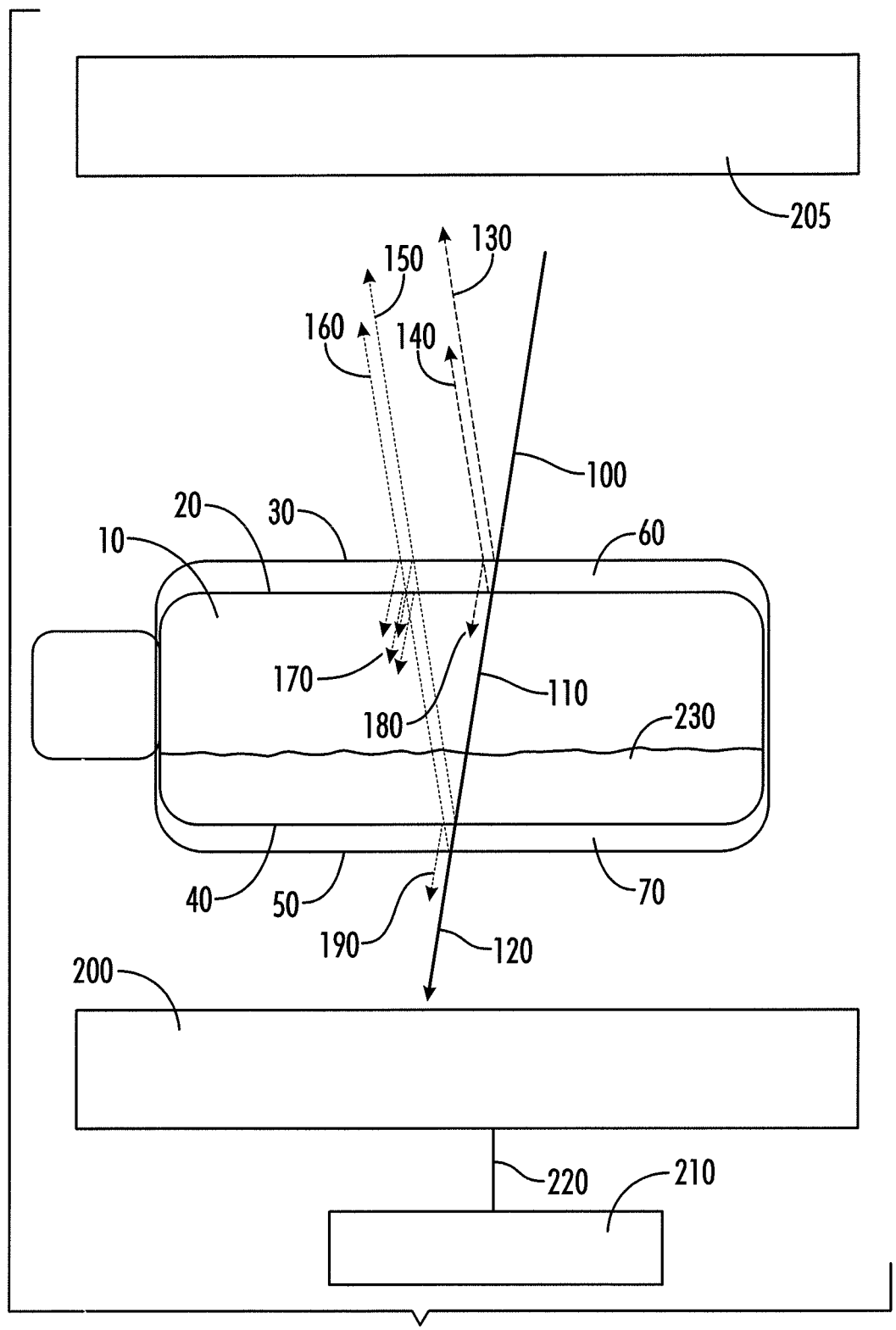
FIG. 14 depicts a schematic diagram similar to FIG. 13. The PET container shown in FIG. 14 contains a liquid, which alters the manner of interaction of the exemplary paths of near infrared radiation with the PET container in this embodiment of the present invention utilizing detection of near infrared radiation transmitted through the walls of the container.

FIG. 2 shows a PET container 10, also called a bottle, like that of FIG. 1 except that it is partially filled with liquid 230, such as water, that mostly absorbs NIR radiation 110 thereby eliminating production of any effective reflected NIR radiation 150 and 160. In this case, only reflected NIR radiation 130 and 140 reach detector system 200 with enough energy to be detected and yield reduced delivery of NIR absorption information derived from one reflection off the container 10 wall 60 surface and from two passes through the container 10 walls 60 to detector system 200 compared to the richer information gained from two reflections and eight passes through container 10 walls 60 and 70 for an empty container 10 (FIG. 1). For the transmissive case (FIG. 14) transmitted NIR radiation 120 is greatly weakened by passage through liquid 230. As a result the detection signal for either the reflective case or the transmitted case from detector system 200 to computer analysis system 210 is weakened both in intensity and in polymer NIR absorption information content making the container 10 containing liquid 230 significantly more difficult to identify correctly than the empty bottle. Again, the herein disclosed invention provides a method to boost the strength of certain polymer NIR absorption features detected by detector system 200 so to improve ability of computer analysis system 210 to make proper identifications of types of materials from the weak detection signals provided by detector system 200.

Referring again to FIG. 1, it can be approximated what happens to the reflected NIR radiations 130, 140, 150, and 160 as PET container 10 walls 60 and 70 become very thin. As discussed earlier, reflections 140, 150, and 160 carry enhanced NIR absorption information on the polymer chemistry of container 10 as a result of passing through container 10 walls 60 and 70. As container walls 60 and 70 become thinner the path length of travel of a radiation beam through the container 10 wall material becomes reduced resulting in less interaction with the container wall material. Consequently the NIR absorption information in the radiation is reduced. Ultimately, as the walls 60 and 70 become so thin to have only a few radiation wavelengths thickness radiation 140 merges into radiation 130 and radiation 160 merges into 150. The net result is that the NIR absorption information content approaches that of radiations in reflection only. This lessening of NIR absorption information content makes detection of the polymer type for thin walled containers more difficult than that for thicker walled containers. Detection of the polymer type for thin walled containers also becomes more difficult than that for thicker walled containers for the transmissive case (FIG. 13) in that transmitted NIR radiation 120 carries less NIR absorption information as the container walls 60 and 70 become thinner. The herein disclosed invention provides a method to boost the strength of such low information content polymer NIR absorption features detected by detector system 200 so to improve ability of computer analysis system 210 to make proper identifications of the type of material from the weak detection signals provided by detector system 200.

The growing use of thin walled PET containers 10 in packaging, including use of such containers 10 to hold bottled water creates a challenge in the recycling industry. First, as earlier discussed, container 10 materials become more difficult to detect as their walls 60 and 70 become thinner. Secondly, the use of these difficult to detect thin walled containers to hold liquids 230 for consumption, such as water bottles, results in many of the containers being capped and discarded while still containing liquid 230, such as water, and show up in the waste stream still holding their liquid 230 contents. The presence of such liquid 230, as earlier discussed, adversely affects the ability of automated sorting systems to correctly identify these containers by polymer type thereby reducing the recycling rate for these polymers.

Figure 3:
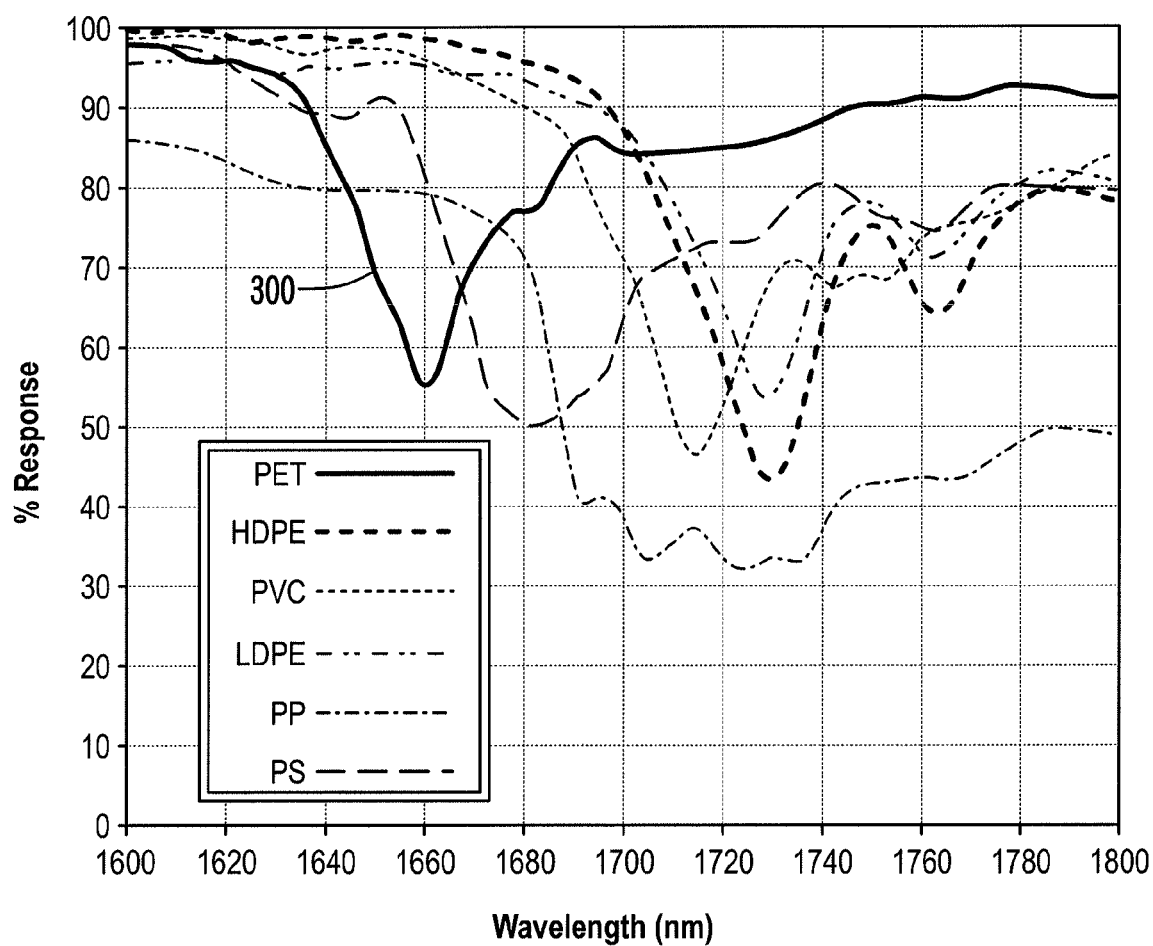
FIG. 3 is a graphical illustration of the near infrared spectra of common plastic packaging materials. Shown therein are PET (solid line), high density polyethylene ("HDPE") (dashed line), polyvinylchloride ("PVC") (dotted line), low density polyethylene ("LDPE") (dash dot dot line), polypropylene ("PP") (dash dot dash line), and polystyrene ("PS") (long dashed line), respectively.

FIG. 3 shows representative NIR spectra in the 1600 nm to 1800 nm range for the most prominent packaging polymers used by manufacturers. Each of the polymers has an absorption spectrum that differs from the other polymers in this wavelength range. Many of the automated infrared based sorting systems in use collect near infrared spectra such as those in FIG. 3 from a stream of materials to be sorted and apply spectral analysis techniques to the spectra to determine polymer types and activate sort mechanisms to sort selected polymers from the stream. Again, such automated sorting systems are well known and readily commercially available. The relative differences between the FIG. 3 spectra for the different polymers are consistent for most common packaging materials and the near infrared based automated sorters perform well in sorting the materials. However, recent advances in materials engineering for polymers has resulted in some of the packaging becoming very thin walled, particularly in the case of PET non-carbonated beverage containers 10 and food containers 10, and also for PE based grocery bags. Of particular interest in this case is the PET spectrum 300.

Figure 4:
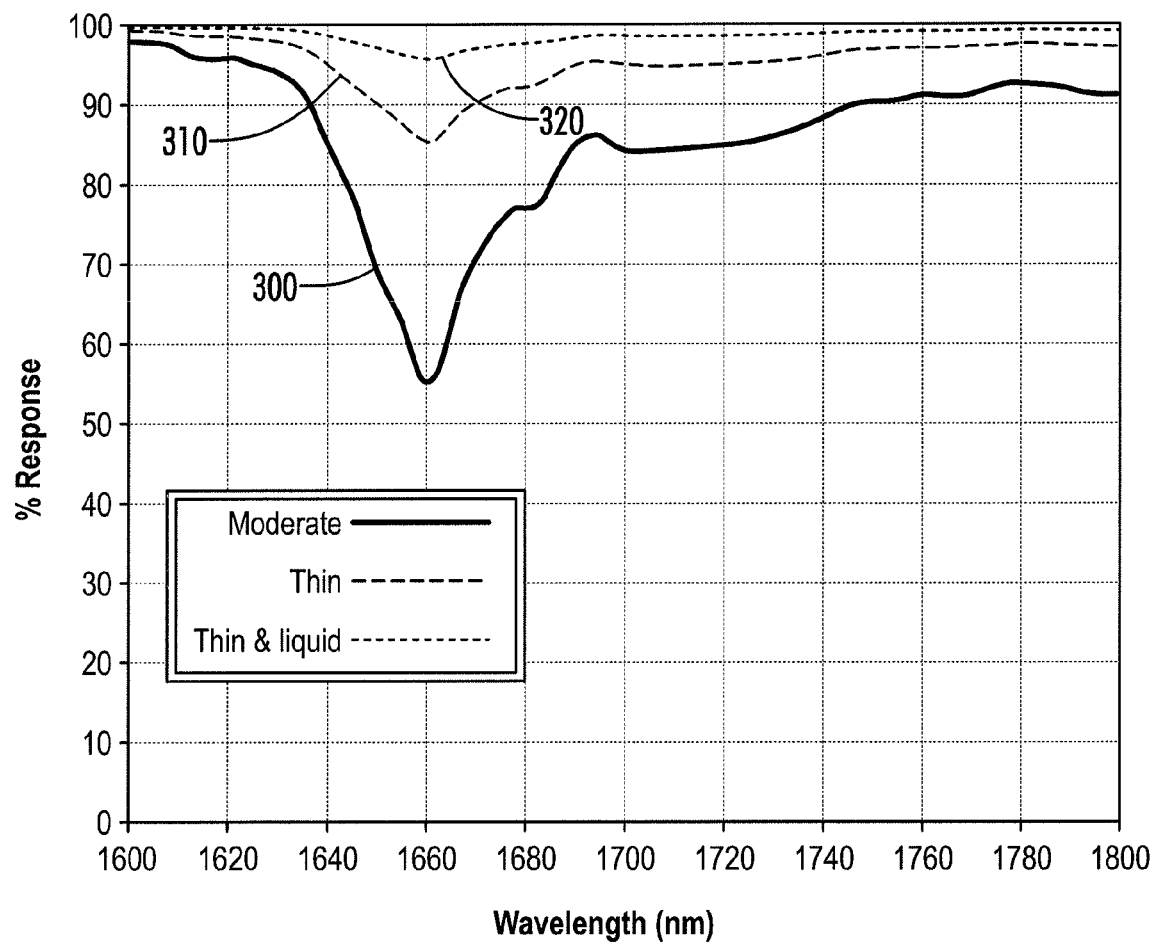
FIG. 4 is a graphical illustration of the near infrared spectra of PET containers with various wall thicknesses and with liquid. Shown therein are PET containers with moderate walls (solid line), thin walls (dashed line), and thin walls and liquid (dotted line), respectively.

FIG. 4 shows relative NIR spectra for PET packaging materials at various wall thicknesses. The spectrum 300 for relatively thick walled material is equivalent in wavelength features and % response of the detectors to spectrum 300 in FIG. 3. Spectra 310 and 320 are identical in wavelength features to spectrum 300 but differ significantly in % response of the detectors to the various levels of NIR radiation producing them due to variations in wall thickness and in the case of 320 also the presence of liquid 230 contents (thin PET bottles containing liquid, such as water, are often referred to in the industry as "wet" PET). A key feature here is that detector system 200 response decreases as wall thickness decreases. The detector system 200 response for spectrum 310 of a thin walled PET container 10 is significantly less than that of a moderate to thick walled PET container 10 spectrum 300. In the case of "wet" PET where there is liquid 230 in a thin walled container 10, such as a thin walled PET container 10 containing water, the detector system 200 response 320 is very low and can approach the noise level of the detectors 200. In such case electronic amplification of the signal is not desirable due to amplification of detector noise which tends to interfere with the spectral measurement.

Figure 5:
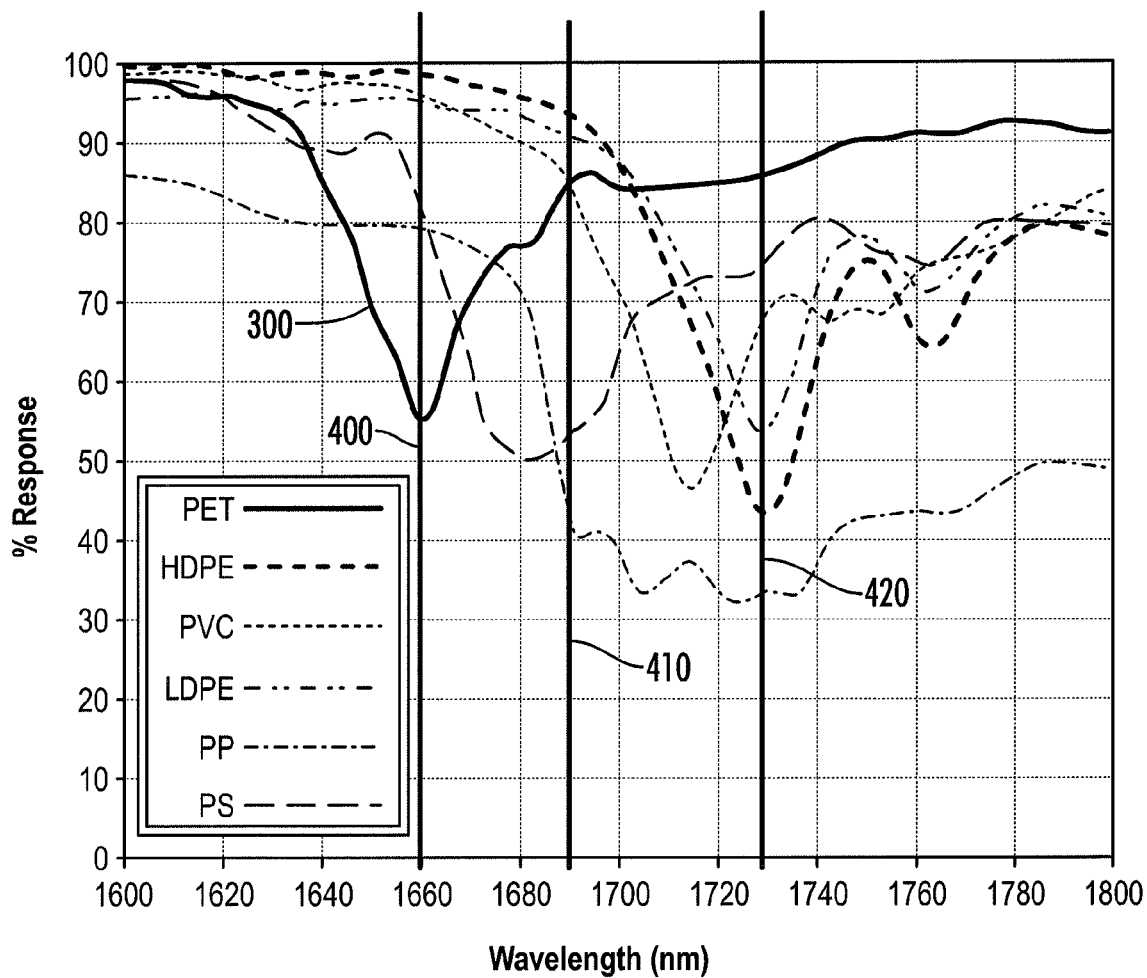
FIG. 5 is a graphical illustration of the near infrared spectra of common plastic packaging materials. Included in the figure are locating lines for reference, which are positioned along the wavelength axis at 1660 nm, 1690 nm, and 1730 nm, respectively. Shown therein are PET (solid line), HDPE (dashed line), PVC (dotted line), LDPE (dash dot dot line), PP (dash dot dash line), and PS (long dashed line), respectively.

FIG. 5 shows the spectra from FIG. 3 with locating lines 400, 410, and 420 positioned along the wavelength axis at 1660 nm, 1690 nm, and 1730 nm respectively for reference. Table 1 below shows relative values of response measured from the chart for the six polymers at each of the reference locating lines at wavelengths 1660 nm, 1690 nm, and 1730 nm.

TABLE 1

NIR DETECTOR PERCENTAGE RESPONSE

| Wavelength | PET | HDPE | PVC | LDPE | PP | PS |
|---|---|---|---|---|---|---|
| 1660 nm | 55.3 | 98.5 | 95.7 | 95.1 | 79.2 | 84.7 |
| 1690 nm | 84.4 | 93.6 | 85.7 | 90.6 | 45.4 | 59.0 |
| 1730 nm | 85.7 | 44.0 | 68.5 | 53.9 | 33.6 | 73.7 |

Looking at Table 1 it can be seen that the NIR detector response for PET at 1660 nm is less than the response at 1690 nm and at 1730 nm. Also it can be seen that the response for the other listed polymers is more at 1660 nm than at 1690 nm or at 1730 nm. It is noted that 1690 nm and 1730 nm have been picked for discussion purposes and that there are other wavelengths that have the same general relationship of PET response to the other polymer's responses. These response relationships reveal that PET can be differentiated from other polymers based on the measurements at 1660 nm compared to measurements at other wavelengths such as 1690 nm and 1730 nm. It is common in today's automated sorting systems to use the response of PET at 1660 nm to identify a polymer as PET.

Figure 6:
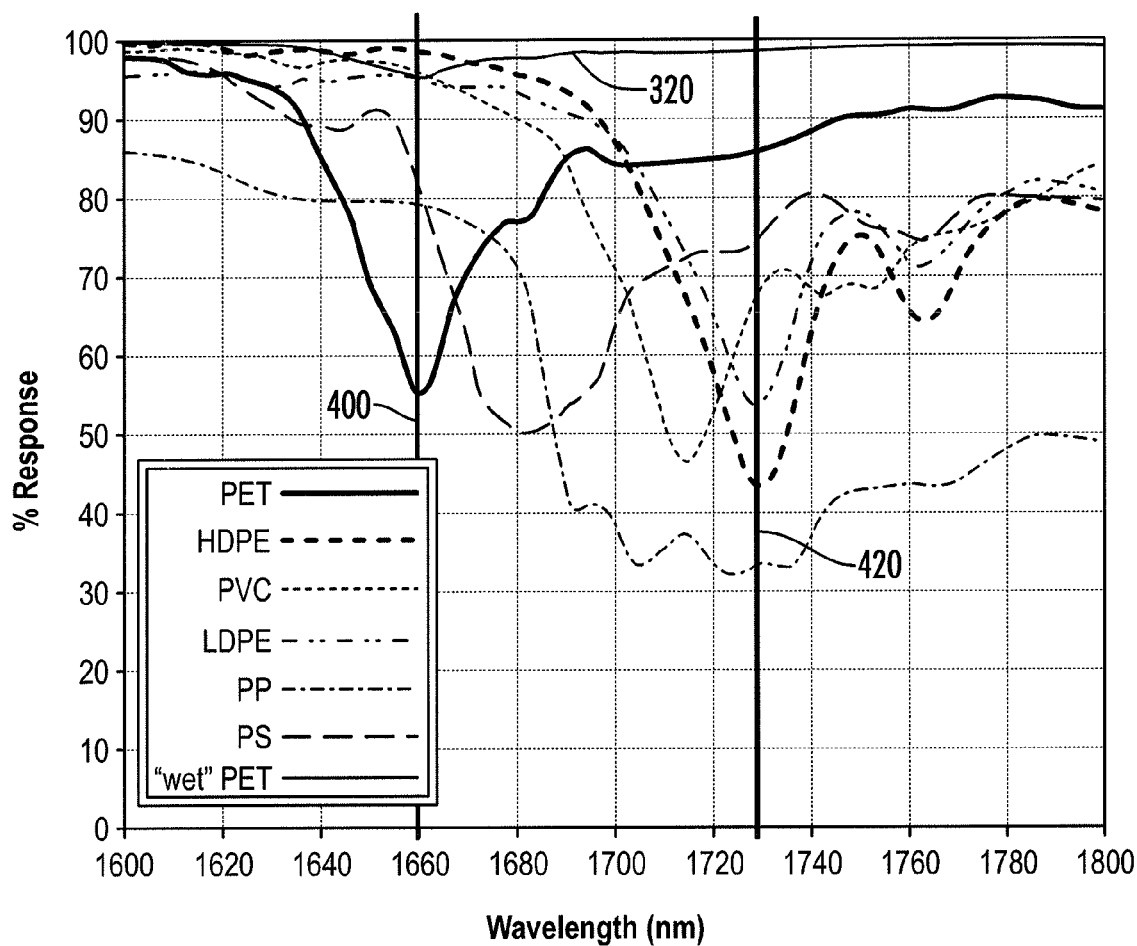
FIG. 6 is a graphical illustration of the near infrared spectra of common plastic packaging materials. Included in the figure are locating lines for reference, which are positioned along the wavelength axis at 1660 nm and 1730 nm, respectively. Shown therein are PET (thick line), HDPE (dashed line), PVC (dotted line), LDPE (dash dot dot line), PP (dash dot dash line), PS (long dashed line), and "wet" PET (thin solid line), respectively.

If the polymer response at 1660 nm is very weak, as in "wet" PET spectra 320 for thin PET containing liquid 230, then it can become difficult to distinguish the absorption feature at 1660 nm from other spectral features and from noise (see FIG. 6). The widely practiced approach to improve such weak signals is to electronically boost the gain of the amplification of the signals from the detection system 200 before they are sent to computer system 210 over connection 220. However, this approach will also amplify the noise in the detection signal and interfering spectra along with the weak PET response such that identification can still be difficult. To solve this problem, the present invention uses a software technique ("boost") to amplify only the PET response after it arrives at computer system 210 having been communicated over connection 220 from detector system 200 without amplifying the accompanying noise and interfering spectra. That is, as further explained below, software is used to force the sorting system to recognize the PET polymer material. The computer 210 uses the "boosted" PET response in providing data to an identification algorithm so to identify the PET polymer even though the PET response by the actual detection system 200 may be very weak. In Table 1 it was demonstrated that the NIR detector 200 response for PET at 1660 nm is always less than the response at 1690 nm and at 1730 nm. Also it was demonstrated that the response for the other listed polymers is more at 1660 nm than at 1690 nm or at 1730 nm. Referring to FIG. 6, in practice then the detector system 200 response at 1660 nm and the detector system 200 response at 1730 nm can measured for any polymer within a stream of polymers or other materials which are to be sorted. Even for very weak detector system 200 responses we have found through experimentation that the general rule that NIR detector system 200 response for PET at 1660 nm is always less than the simultaneous response at 1730 nm. Similarly we have found through experimentation that among the common packaging polymers the detector system 200 response is more at 1660 nm than the simultaneous response at 1730 nm for polymers other than PET. Importantly we have also found that for other common waste stream materials such as paper, wood, cardboard, Tetrapak, and gable cartons the detector system 200 response is more at 1660 nm than the simultaneous response at 1730 nm. A minor exception is for aluminum cans where the responses are almost equal, ie. $R(u)=0.97\sim1$. Table 2 summarizes these measurements.

TABLE 2

Detector response at 1660 nm divided by detector response at 1730 nm

| Material | R(u) |
|---|---|
| HDPE COLOR | 4.47 |
| PVC | 2.05 |
| PP CLEAR | 2.28 |
| PS | 1.16 |
| OTHER (7) | 2.27 |
| PAPER | 1.09 |
| CARDBOARD | 1.05 |
| WOOD | 1.03 |
| AL CAN | 0.97 |
| TETRA PAK | 1.13 |
| MILK (GABLE) | 1.20 |
| THIN PET EMPTY | 0.86 |
| THIN PET 1 oz water | 0.88 |
| THIN PET 2 oz water | 0.89 |
| THIN PET 8 oz water | 0.94 |
| THICK PET EMPTY | 0.71 |
| PET G (BLUE) | 0.66 |

In Table 2 the measurements and the comparisons are after normalization of the detection system signals. The normalization step of adjusting detector outputs so that they each give the same output response when measuring reflected radiation from a neutral material type that has equal absorption characteristics at all wavelengths being detected is well known to one of ordinary skill in the art. In Table 2 R(u) is the ratio of measured normalized detector response at 1660 nm to measured normalized detector response at 1730 nm. To be clear, normalized NIR detector responses were obtained at 1660 nm and 1730 nm for the listed materials. The percent detector response at 1660 nm was divided by the percent detector response at 1730 nm to obtain a ratio—R(u) as listed in Table 2.

Referring to Table 2 it can be seen that the R(u) value for PET is less than 0.95 while the R(u) value is greater than 0.95 for other materials and polymers. We refer to the 0.95 value in this example as the "Boost Threshold," also called preset threshold, such that if R(u) is less than or equal to the Boost Threshold then we assume the material being examined is PET and a software amplification (to be discussed below) is applied to boost the spectral signal. If R(u) is greater than the Boost Threshold then it is assumed that the material is not PET and no software amplification is applied. In practice we have found that the Boost Threshold for measurements at these wavelengths can be set anywhere between 0.82 to 0.95 to effect enhanced identifications of PET with the upper value of 0.95 being the most sensitive setting and 0.82 being the least sensitive setting. It is noted that the value of the Boost Threshold is dependent upon the spectral wavelengths being compared and that it has values different than these, for instance, when using measurements at 1660 nm compared to measurements at 1690 nm. For example, in another embodiment, R(u) is the ratio of measured normalized detector response at 1660 nm to measured normalized detector response at 1690 nm.

Figure 7:
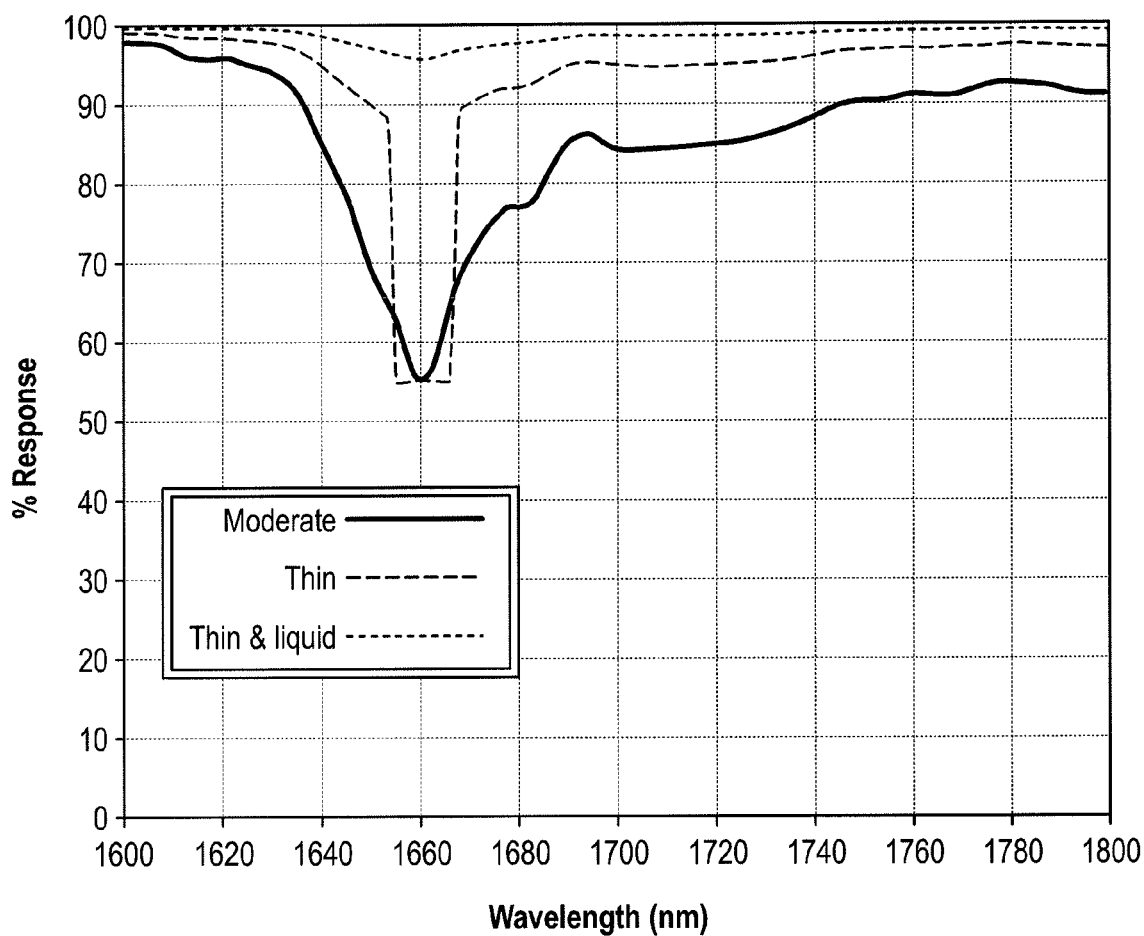
FIG. 7 is a graphical illustration of the near infrared spectra of PET containers with various wall thicknesses and with liquid. Shown therein is an exemplary forced response due to one method of forcing a spectral response over a 10 nm region centered at 1660 nm for a weak signal resulting from a thin walled PET container (dashed line). Also shown are the regular spectral responses for PET containers with moderate walls (solid line) and thin walls and liquid (dotted line), respectively.
Figure 8:
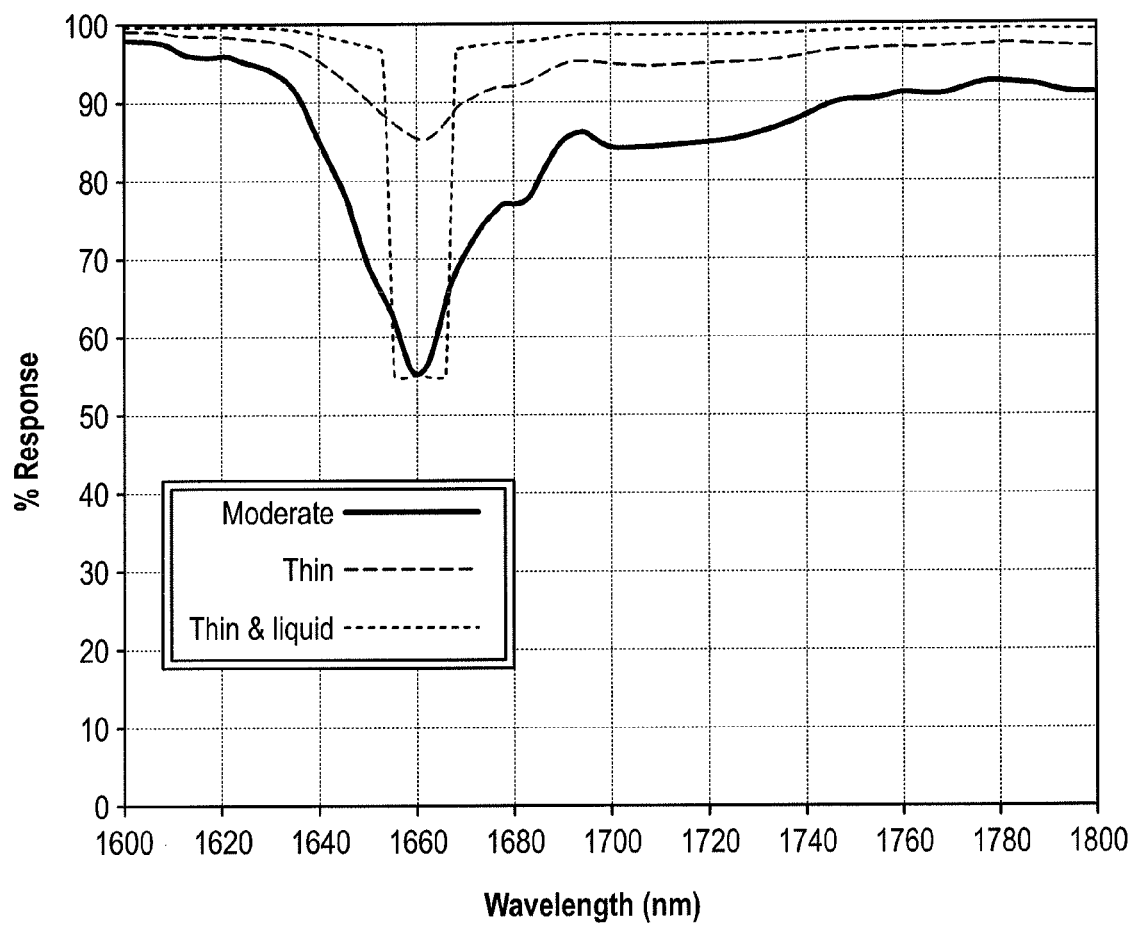
FIG. 8 is a graphical illustration of the near infrared spectra of PET containers with various wall thicknesses and with liquid. Shown there is an exemplary forced response due to one method of forcing a spectral response over a 10 nm region centered at 1660 nm for a weak signal resulting from a thin walled PET container containing liquid (dotted line). Also shown are the regular spectral responses for PET containers with moderate walls (solid line) and thin walls (dashed line), respectively.
Figure 9:
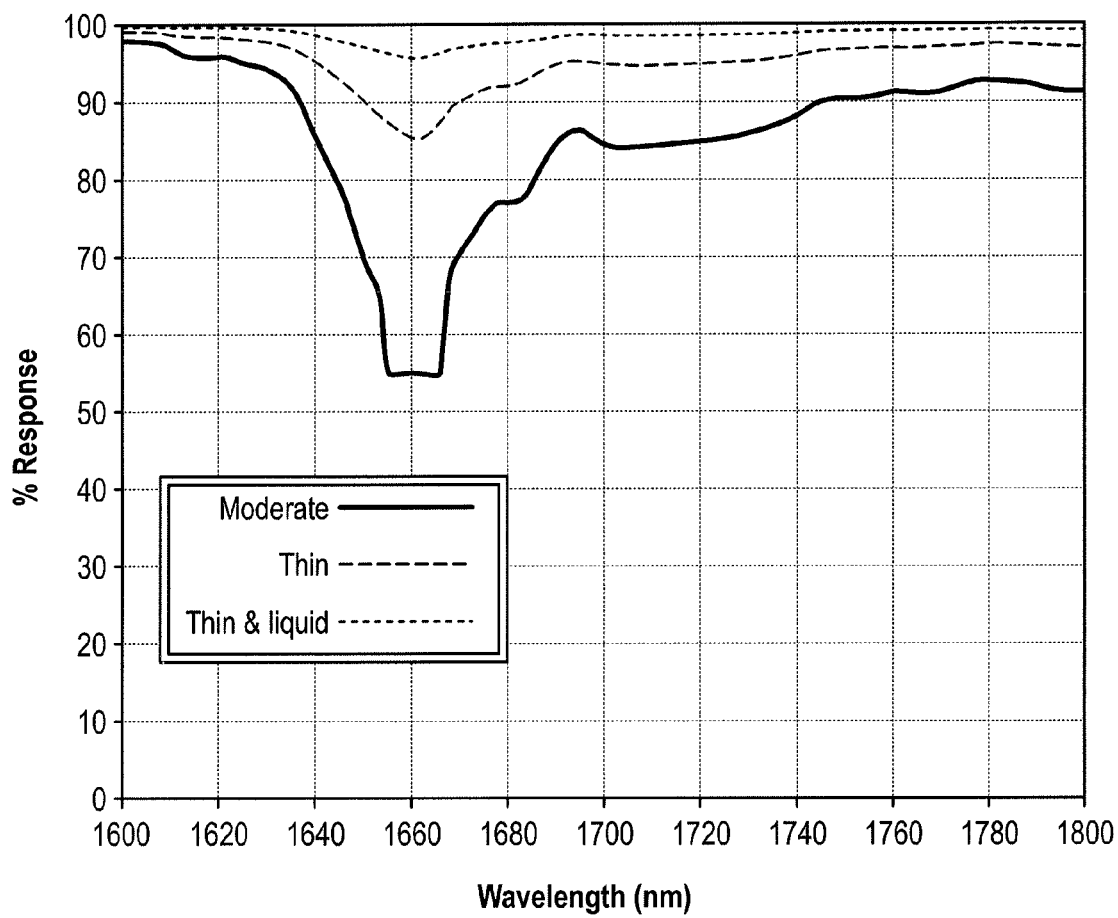
FIG. 9 is a graphical illustration of the near infrared spectra of PET containers with various wall thicknesses and with liquid. Shown there is an exemplary forced response due to one method of forcing a spectral response over a 10 nm region centered at 1660 nm for a signal resulting from a moderate walled PET container (solid line). Also shown are the regular spectral responses for PET containers with thin walls (dashed line) and thin walls and liquid (dotted line), respectively.
Figure 10:
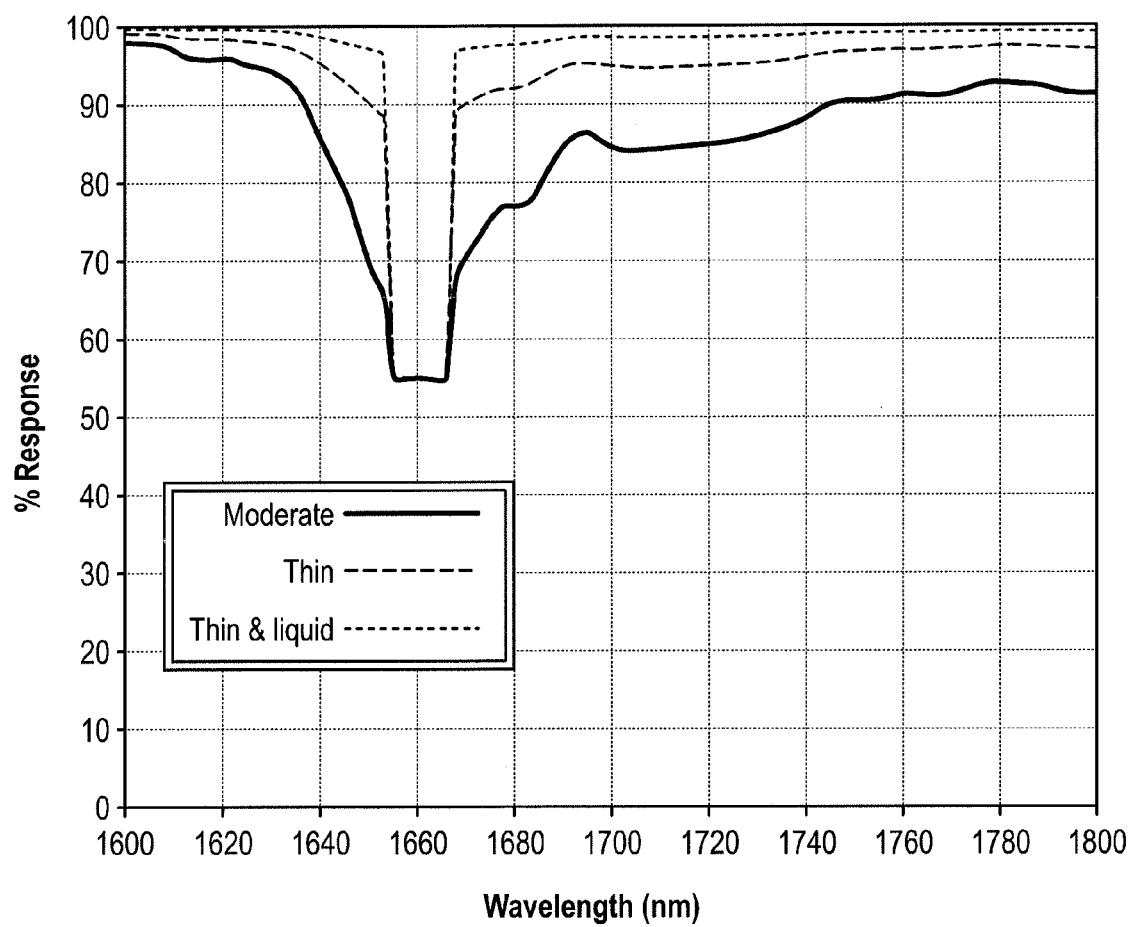
FIG. 10 is a graphical illustration of the near infrared spectra of PET containers with various wall thicknesses and with liquid. Shown there is an exemplary forced response for each of the shown spectral responses over a 10 nm region centered at 1660 nm. Each of the spectral responses has been forced to a value of 55% (for example). Shown there are for a signal resulting from a moderate walled PET container (solid line). Shown therein are PET containers with moderate walls (solid line), thin walls (dashed line), and thin walls and liquid (dotted line), respectively.

In the present invention the software technique applied to "boost" the PET detection response is to process the spectral data in computer 210 arriving from detector system 200 over connection 220 in the 1660 nm region and the 1730 nm region and if the R(u) value is less than or equal to a pre-set Boost Threshold then replace the measured detector system 200 response received by computer 210 in the 1660 nm region with a "forced" boost response so that the spectral signal as processed by the identification algorithm within computer 210 resembles a robust spectral response 300. FIG. 7 shows a depiction of the result of one method of applying the boost forced response wherein values of the spectral response over a 10 nm region centered at 1660 nm are forced to a value of 55% (for example) for a weak signal resulting from a thin walled PET material. Similarly FIG. 8 shows a depiction of the result of applying the boost forced response wherein values of the spectral response over a 10 nm region centered at 1660 nm are forced to a value of 55% (for example) for a weak signal resulting from a thin walled PET bottle containing liquid. FIG. 9 shows what happens with a robust PET signal from a PET material having moderately thick walls when processed through the boost forced response application. In such case the PET signal shows only slight effects from applying the boost forced response. FIG. 10 depicts application of the boost function to all three spectral signals graphed. The FIG. 7, FIG. 8, FIG. 9, and FIG. 10 examples depict NIR detection signals where the boost function applied has a "square wave" shape over the wavelength region of application. Other shapes could similarly be applied such as a V shape, a parabolic shape, a semi-circular shape, etc. as needed for good performance with the identification algorithm that will analyze the spectra and make a decision as to what type of polymer is present.

Figure 11:
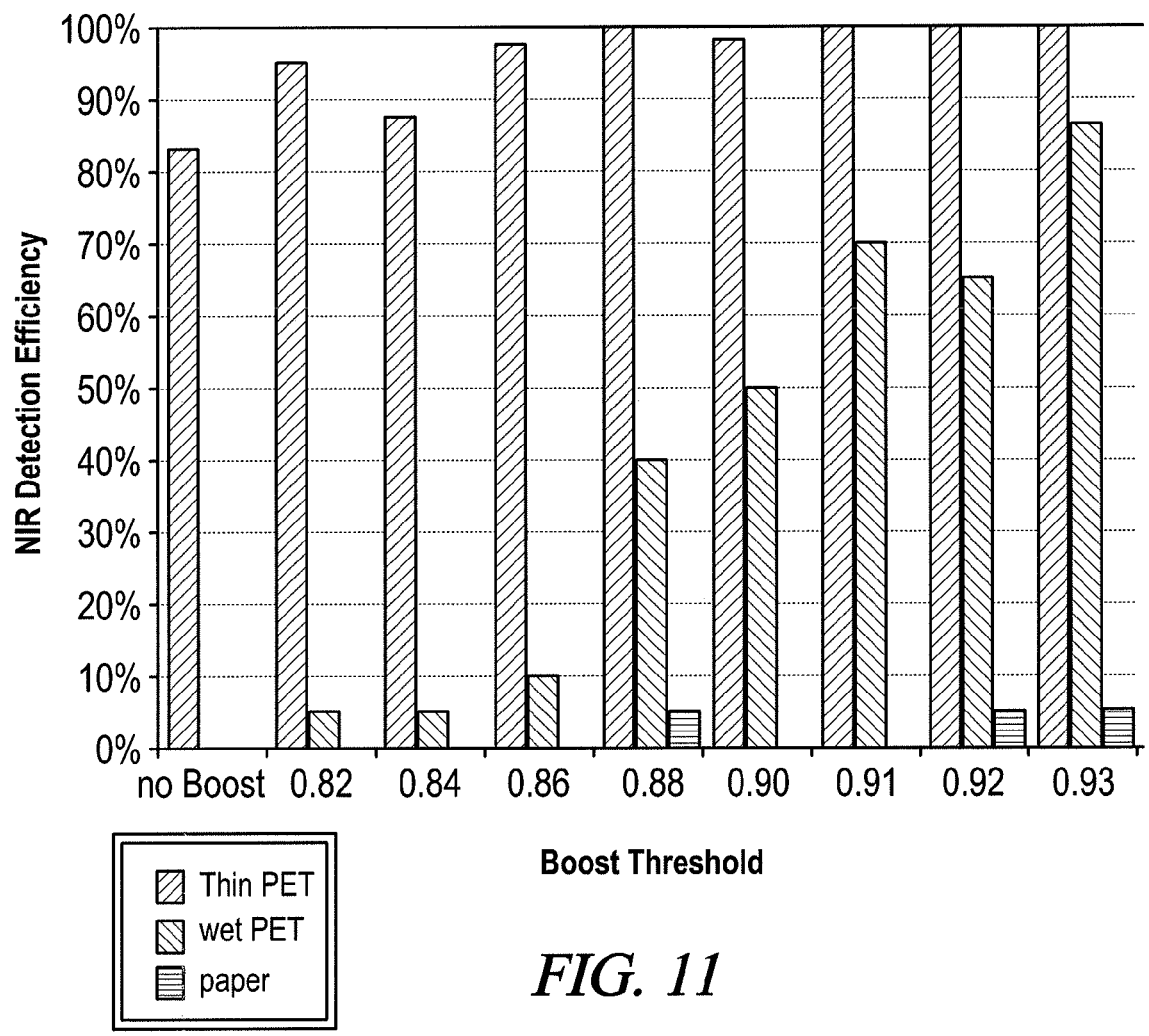
FIG. 11 is a bar graph illustration of data from use of an embodiment of the invention to show the detection efficiency of PET materials with and without forcing spectral responses to alternate values in order to enhance detection. Shown therein are results for thin walled PET containers (hatching angled to the right), "wet" PET containers (hatching angled to the left) and paper (horizontal hatching).

FIG. 11 shows a graph of experimental data taken on the effectiveness of identification of PET materials and false identifications of paper as PET by an identification algorithm without and with application of the new boost technology to reflection NIR signals received from a detection system prior to processing the NIR signals through the identification algorithm. It is desired that all PET materials be identified without any false identifications of non-PET materials in the waste stream. Testing has showed that when using NIR reflection technology paper is the most likely non-PET material in the waste stream to be falsely identified as a PET material when applying the boost technology so the graph shows PET identifications along with paper identifications for various values of Boost Threshold from no boost up to a value of 0.93. Above 0.93 it was found for the configuration being tested that paper identifications rose to above 5% which is not desirable in order to have a clean PET product in operation. It is noted that when using NIR transmission technology false identifications of NIR opaque items such as metals, paper, wood, opaque plastics, etc. is typically not a problem since they do not transmit at NIR wavelengths. In such transmissive cases the Boost Threshold for the percent detector response at a region about 1660 nm divided by the percent detector response at a region about 1730 nm can be elevated above 0.95 to a higher number, for example 0.98. It has been found in operation of NIR based sorters deployed in industrial applications that thin walled PET bottles having liquid in them (wet PET) are generally not detected by the sorters while thin walled PET containers without liquid are detected to varying degree depending upon the sensitivity settings of the sorter. In general we have found that if sensitivity settings are set high enough to optimize recovery of thin walled PET then too much contamination is falsely sorted along with the PET material. For the data in FIG. 11 the sorting system was set at a fairly high sensitivity setting to maximize thin PET identification without using the new boost technology. In that case thin PET was detected at about a 80% efficiency while no wet PET was detected. With boost technology enabled and at a Boost Threshold of 0.82 thin PET detection was improved to about 95% and about 5% of wet PET detected. As the Boost Threshold was increased detection efficiencies improved significantly so that at Boost Threshold=0.93 there was a greater than 85% detection efficiency for wet PET (thin PET bottles about ¼ full of liquid) and a 100% detection efficiency for thin PET while maintaining false detections of paper to 5% and below.

Figure 12:
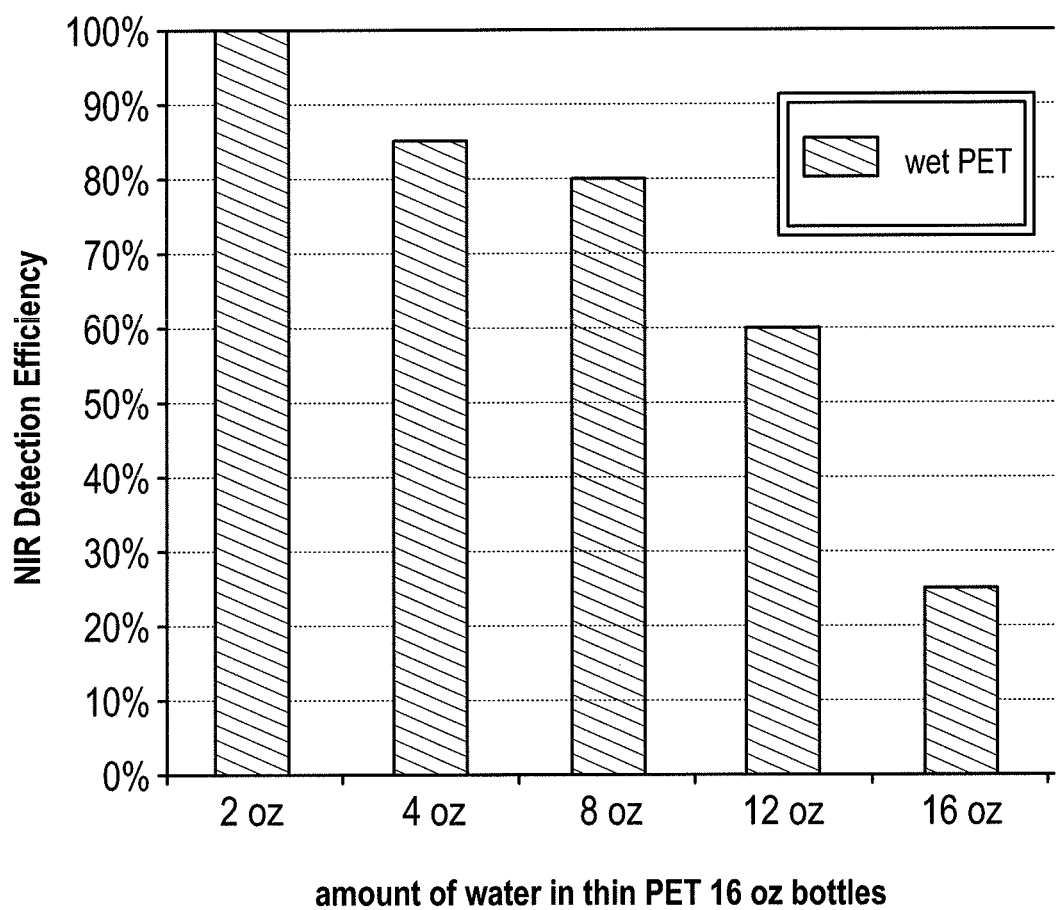
FIG. 12 is a bar graph illustration of the efficiency of detection of "wet" PET in relation to the amount of liquid in a thin walled PET container. As the amount of liquid increases, the efficiency of detection decreases.

FIG. 12 shows detection efficiency of wet PET as a function of the amount of liquid in a thin PET bottle. It is shown there that as the amount of liquid contained in a thin walled PET bottle increases detection of the bottle as PET becomes more difficult.

While measuring effectiveness of PET detection using the boost methodology disclosed herein it was found that paper in the waste stream could present a significant problem due to a tendency to get a false identification as a PET material from NIR signals reflected off of paper. Further investigation revealed that the level of NIR signals reflected off paper, cardboard, or other fibrous materials is consistently greater than the level of NIR signals reflected off PET materials with measurements indicating that, in general, paper is about twice as "bright" as PET materials. Preliminary algorithms were developed and tested to look at the level of NIR signals reflected off of materials and if a signal was above a preset threshold, or if the rate of rise of a signal was above a preset threshold, then an override of a PET determination by the materials identification algorithm was invoked so to lessen the incidence of false PET identifications of paper items. Testing showed this approach to be promising in preventing false PET identifications induced by boosting of paper signals and even false identifications of paper as PET materials when not using the boost technology.

All references, publications, and patents disclosed herein are expressly incorporated by reference.

Thus, it is seen that the method of the present invention readily achieves the ends and advantages mentioned as well as those inherent therein. While certain preferred embodiments of the invention have been illustrated and described for purposes of the present disclosure, numerous changes in the arrangement and construction of parts or arrangement of steps may be made by those skilled in the art, which changes are encompassed within the scope and spirit of the present invention as defined by the following claims.

What is claimed is:

1. A method of improving detection of polyethylene terephthalate polymer materials within a stream of materials comprising:
   providing a stream of materials;
   irradiating the stream of materials with near infrared radiation;
   measuring near infrared radiation emanating from the stream of materials;
   analyzing the measured near infrared radiation at two or more wavelength regions;
   determining a ratio of measured near infrared radiation at two regions of wavelengths;
   comparing the ratio to a preset threshold;
   adjusting the measured near infrared radiation measurements at one of the wavelength regions according to the results of the comparing step;
   wherein adjusting the measured near infrared radiation measurements at one of the wavelength regions is adjusting the measured near infrared radiation measurements at one of the wavelength regions to boost the measured near infrared radiation measurements at one of the wavelength regions;
   processing the adjusted near infrared radiation measurements;
   identifying at least one polyethylene terephthalate polymer material.

2. The method of claim 1, wherein the stream of materials contains at least one material item of polyethylene terephthalate polymer.

3. The method of claim 2, wherein the wavelength regions include a region located at about 1660 nm.

4. The method of claim 3, wherein the ratio is determined for wavelength regions including a region located at about 1660 nm.

5. The method of claim 4, wherein adjusting the measured near infrared radiation measurements further comprises adjusting the near infrared radiation measurement for a region located at about 1660 nm.

6. The method of claim 5, wherein the wavelength regions include a region located at about 1730 nm.

7. The method of claim 6, wherein the preset threshold is a value between 0.8 and 0.98.

8. The method of claim 7, further comprising separating the identified polyethylene terephthalate polymer material from the stream of materials.

9. The method of claim 5, wherein the wavelength regions include a region located at about 1690 nm.

10. The method of claim 9, wherein the preset threshold is a value between 0.8 and 0.98.

11. The method of claim 10, further comprising separating the identified polyethylene terephthalate polymer material from the stream of materials.

12. The method of claim 1, wherein adjusting the measured near infrared radiation measurements at one of the wavelength regions is adjusting the measured near infrared radiation measurements at one of the wavelength regions to make the measured near infrared radiation measurements at the one of the wavelength regions resemble a robust spectral response for polyethylene terephthalate polymer materials when the determined ratio is less than or equal to the preset threshold.

* * * * *